United States Patent
Ronkainen et al.

(10) Patent No.: US 6,477,397 B1
(45) Date of Patent: Nov. 5, 2002

(54) ELECTRODE STRUCTURE

(75) Inventors: Ilkka Ronkainen, Oulu; Jarmo Lehtonen, Turku, both of (FI)

(73) Assignee: Polar Electro Oy, Kempele (FI)

(*) Notice: Subject to any disclaimer, the term of this patent is extended or adjusted under 35 U.S.C. 154(b) by 0 days.

(21) Appl. No.: 09/574,147

(22) Filed: May 18, 2000

(30) Foreign Application Priority Data

May 20, 1999 (FI) .............................. 990232 U

(51) Int. Cl.$^7$ ................................ A61B 5/04

(52) U.S. Cl. ...................... 600/390; 600/393

(58) Field of Search ................ 600/372, 382, 600/386, 388, 389, 391, 392, 393, 390, 509; 607/152

(56) References Cited

U.S. PATENT DOCUMENTS

| | | | | |
|---|---|---|---|---|
| 4,226,247 A | * | 10/1980 | Hauser et al. | 600/372 |
| 4,690,148 A | * | 9/1987 | Hess | 600/372 |
| 4,969,468 A | * | 11/1990 | Byers et al. | 600/393 |
| 6,002,957 A | * | 12/1999 | Finneran | 600/372 |
| 6,004,312 A | * | 12/1999 | Finneran et al. | 600/382 |

* cited by examiner

Primary Examiner—Linda C. M. Dvorak
Assistant Examiner—David M. Ruddy
(74) Attorney, Agent, or Firm—Hoffman & Baron, LLP

(57) ABSTRACT

The invention relates to an electrode structure for measuring a biosignal from a living body, which electrode structure comprises a contact surface intended to be placed against the body. It is essential for the invention that the contact surface comprises several adjacent wave fronts, which wave fronts comprise protrusions and valleys, which are situated lower between the protrusions.

18 Claims, 3 Drawing Sheets

Sectional view from A to A

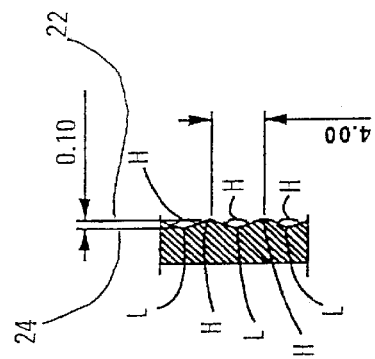
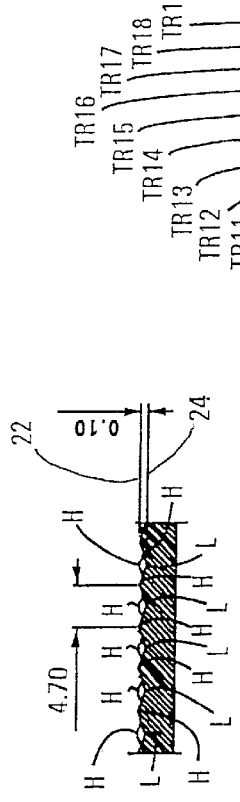
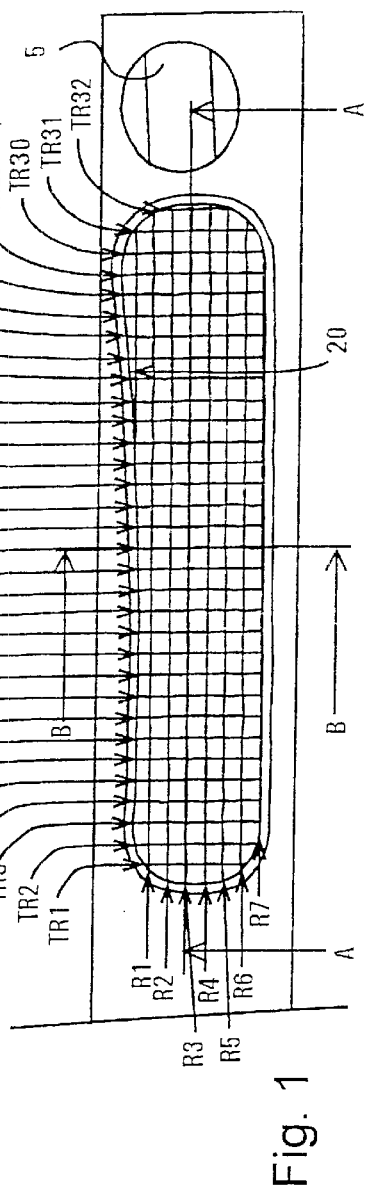

ELECTRODE STRUCTURE

BACKGROUND OF THE INVENTION

1. Field of the Invention

Field of the invention relates to an electrode structure for measuring a biosignal from a living body, which electrode structure comprises a contact surface intended to be placed against the body.

2. Brief Description of the Related Art

The invention is particularly applied in a non-invasively measuring, personal heart rate measuring arrangement, in an electrode belt, or a so-called transmitter belt, of the heart rate measuring arrangement, the belt being in a wireless connection with a receiver unit, in most cases a wristband unit. The electrode belt need not necessarily be a transmitter, but it may just be a measuring unit as well, if it is equipped with a display or a memory, for example.

In known electrode structures of electrode belts, there are long continuous protrusions next to each other on the contact surface, and they are either direct or they wind in the direction of the surface. In both known electrode structures, each protrusion is long, continuous and equally thick.

The known solutions are associated with drawbacks concerning particularly the quality of the contact caused by the electrode against the skin. Since a protrusion is continuous, each continuous protrusion only creates one long contact surface, and the contact between the long continuous protrusion and the skin is not especially strong. It is obvious that a weak contact between the surface of the electrode structure and the skin may lead to errors in the measurement results.

BRIEF DESCRIPTION OF THE INVENTION

The object of the invention is thus to provide a new electrode structure avoiding the problems and drawbacks associated with the known solutions.

To achieve the above object, the electrode structure of the invention is characterized in that the contact surface comprises several adjacent wave fronts, which wave fronts comprise protrusions and valleys, which are situated lower between the protrusions.

The invention is based on the idea that an electrode surface is shaped in a way that improves the quality of the contact between the surface of the electrode structure and the skin.

The electrode structure of the invention provides the advantage that the contact between the electrode surface and the skin improves. The invention provides a large number of contact points with small surface areas for use, each of which contact points effects a stronger point contact. By means of a better contact, reliable measurement results free of interference can be achieved. The preferred embodiments of the invention and other embodiments described later in greater detail make the advantages of the invention more significant. Proceeding wavelike and comprising at least to some extent curved protrusions and valleys, each wave front and thus the entity of several wave fronts feel good against the skin and are easier to keep clean as well, since the protrusions change slowly into valleys and vice versa.

BRIEF DESCRIPTION OF THE DRAWINGS

In the following the invention will be described in greater detail in connection with the preferred embodiments with reference to the attached drawings, in which FIG. 1 shows a belt-like measuring and/or transmitter unit from the area of an electrode by means of a chart illustrating the shape of a contact surface of the electrode, FIG. 3 shows a sectional view from A to A of FIG. 1, FIG. 4 shows a sectional view from B to B of FIG. 1.

DETAILED DESCRIPTION OF THE INVENTION

Figure 2:
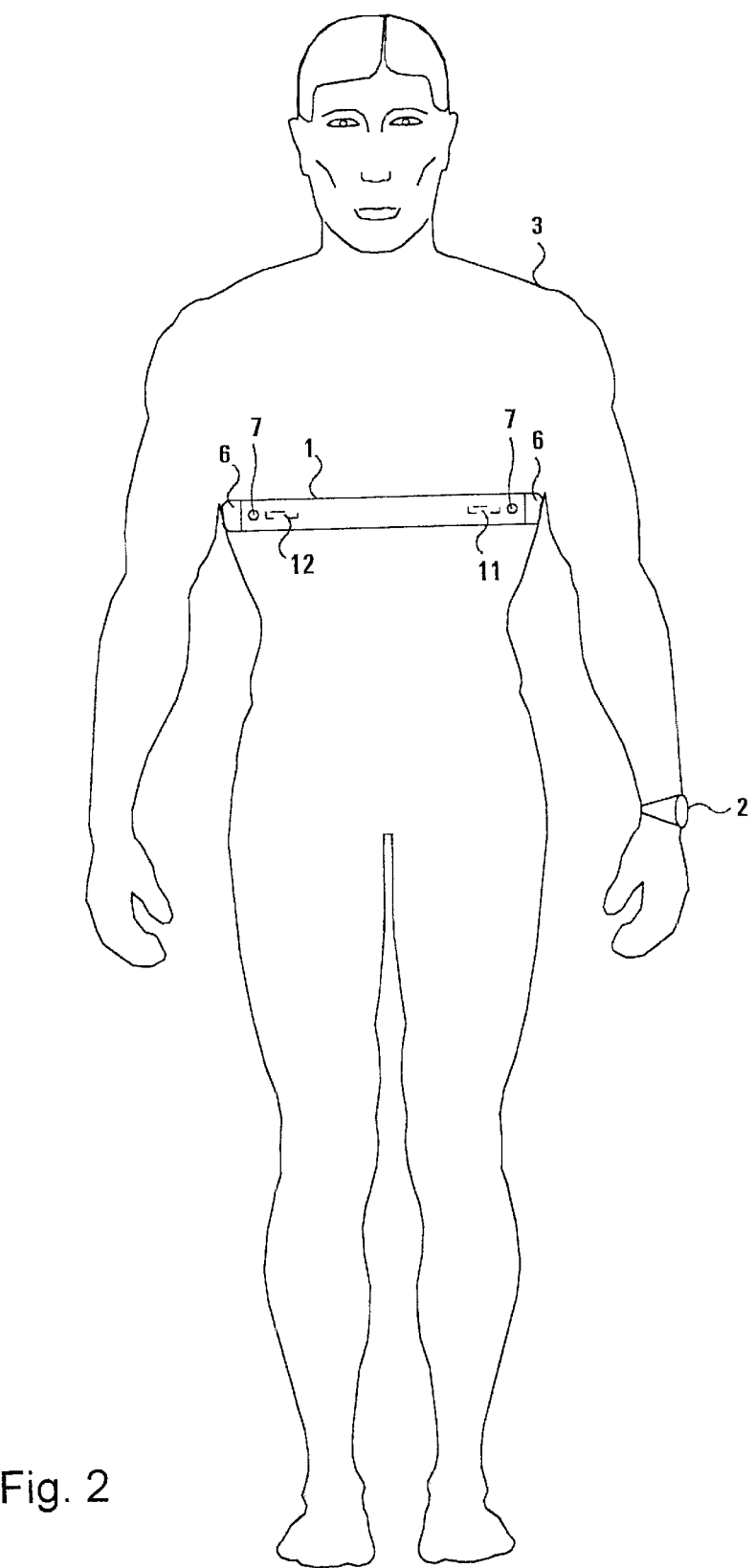
FIG. 2 shows a belt-like transmitter unit at a person's chest, comprising two electrode structures, and a receiver unit at a person's wrist.

Referring first to FIGS. 1 and 2 in particular, it is to be stated that the invention is particularly applied to a non-invasively measuring personal heart rate measuring arrangement 1, 2, which is used by e.g. sport enthusiasts and athletes or other people 3. The heart rate measuring arrangement comprises two units: a heart rate information transmitter unit 1, generally of a transmitter belt type, comprising EKG electrodes 11 to 12, i.e. electrode structures 11 to 12, and a receiver unit 2 formed e.g. as a wristband, including e.g. a microprocessor, display and user interface (not shown) and being in a telemetric inductive connection or an optical or other connection, e.g. in an RF connection, with the heart rate information transmitter unit. The transmitter belt 1 does not transmit a heart rate value, but burst-like information on the heart rate, and using this information, the receiver 2 calculates by means of a microprocessor some other calculating unit the value of the heart rate to be shown on the display.

The present invention relates thus to a transmitter unit 1. On the other hand, if the calculating unit, such as a microprocessor, and possibly the display were integrated to the same entity as the electrodes 11 to 12, it would not actually deal with a transmitter unit 1 any more, but, expressed with a more general term, with a measuring unit 1. The invention is applicable to both of the above versions, independent of whether the heart rate measuring arrangement is a conventional one with two units or whether it is integrated to one entity. Referring to FIGS. 1 and 2, an opening 5 is a locking case for a locking projection 7 at the end of the strap 6 of the electrode belt 1.

In the following mainly the electrode 11 is discussed, as the electrode 12 is exactly similar.

The invention relates thus to an electrode structure 11 for measuring a biosignal, especially a heart rate, from a living body 3, which electrode structure 11 comprises a contact surface 20 intended to be placed against the body 3, and the invention relates to the surface shape of that contact surface in particular, as the contact surface 20 comprises several adjacent wave fronts R1 to R7, which wave fronts R1 to R7 comprise protrusions H and valleys L, which are situated lower between the protrusions H. The protrusions and valleys can most clearly be seen from FIGS. 3 to 5. The wave fronts R1 to R7 are such that each wave front R1 to R7 is preferably a front formed of successive and alternating protrusions H and valleys L. In the figures the wave fronts R1 to R7 proceed preferably in the longitudinal direction of the transmitter belt, ie. also in the longitudinal direction of the electrode. Preferably the contact surface 20 is an electrically conducting material, and is curved at the peak of each protrusion. Referring to FIG. 3, preferably the adjacent wave fronts have a substantially sinusoidal form so that the protrusions define an upper level 22 and the valleys define a lower level 24. Preferably the sinusoidal form has a ratio of wavelength over amplitude in a range from about 75 to 100 where the wavelength is substantially equal to the distance between two peaks and the amplitude is substantially equal to half the distance between the upper level 22 and the lower level 24. Most preferably the sinusoidal form has a ratio of wavelength over amplitude of about 94.

In a preferred embodiment, the contact surface 20 comprises wave fronts TR1 to TR32 with protrusions H and valleys L, the wave fronts being transversal to the wave fronts R1 to R7. Thus, in the preferred embodiment the contact surface 20 is such that the protrusions H and the valleys L of the wave fronts R1 to R7 are arranged in such a manner that the protrusions H and the valleys L of the wave fronts R1 to R7 form wave fronts TR1 to TR32 transversal to the wave fronts R1 to R7, in which the protrusions H and the valleys L alternate. The structure may alternately be such that the peaks H of the wave fronts R1 to R7 are the peaks of the transversal wave fronts TR1 to TR32 as well, which is the case in the above version, but the valleys L of the transversal wave fronts TR1 to TR32 would be different than the valleys L of the wave fronts R1 to R7. Referring to FIG. 4, preferably the transversal wave fronts have a substantially sinusoidal form so that the protrusions define an upper level 22 and the valleys define a lower level 24. Preferably the sinusoidal form has a ratio of wavelength over amplitude in a range from about 75 to 100 where the wavelength is substantially equal to the distance between two peaks and the amplitude is substantially equal to half the distance between the upper level 22 and the lower level 24. Most preferably the sinusoidal form has a ratio of wavelength over amplitude of about 80.

Figure 5:
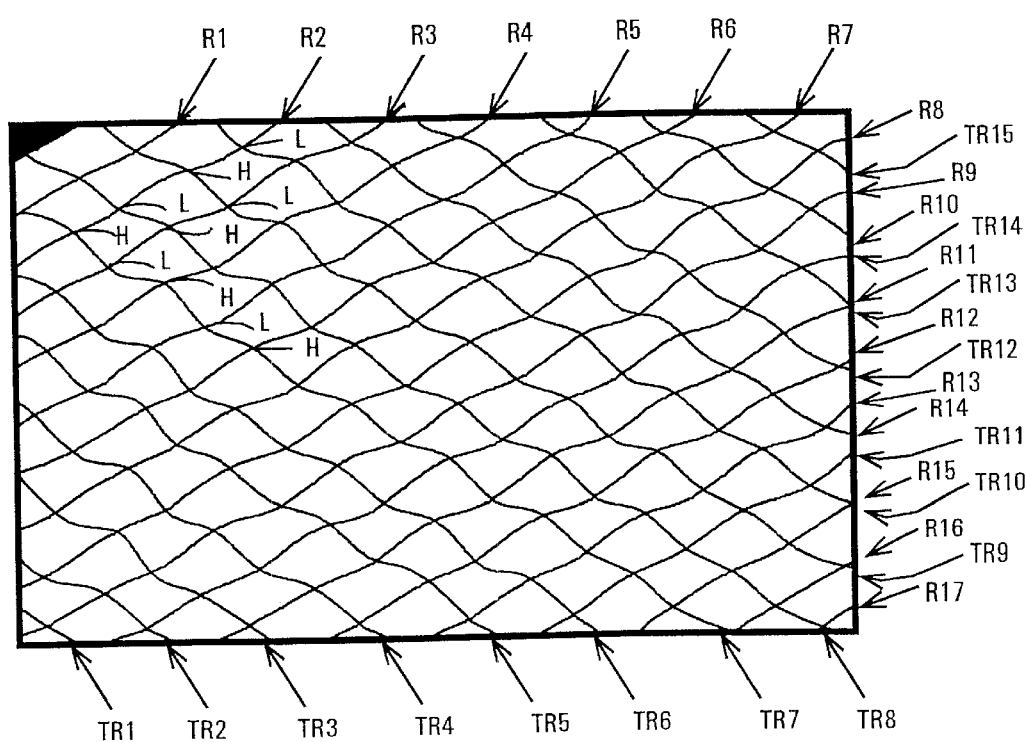
FIG. 5 shows a perspective view of an area on a contact surface of the electrode by means of a chart illustrating the shape of a contact surface of the electrode.

To illustrate the shape of the contact surface 20, FIGS. 1 and 5 show a chart, which is naturally not present in reality. The horizontal lines of the chart in FIG. 1 and the chart lines in the direction from 2 to 8 clock in FIG. 5 illustrate wave fronts R1 to R7 (in FIG. 5, wave fronts R1 to R17) such that the line follows that route of the wave front which goes from the peak of the protrusion H to the bottom of the valley L and again to the peak of the next protrusion H etc. Correspondingly, the vertical lines of the chart in FIG. 1 and the chart lines in the direction from 10 to 4 o'clock in FIG. 5 illustrate transversal wave fronts TR1 to TR32 (in FIG. 5, the wave fronts TR1 to TR15) such that the line follows the route of the transversal wave front that goes from the peak of the protrusion H to the bottom of the valley L and again to the peak of the next protrusion H etc.

In FIG. 1, the transversal wave fronts R1 to R7 proceed in the transverse direction of the transmitter belt, i.e. also in the transverse direction of the electrode belt. In a preferred embodiment, the transversal wave fronts TR1 to TR20 are perpendicularly transversal to the wave fronts R1 to R7, i.e. almost 90 degrees.

In a preferred embodiment, the protrusions H of the adjacent wave fronts in the wave fronts R1 to R7, e.g. the wave fronts R3, R4, are not opposed to each other, i.e. the protrusions H of the adjacent wave fronts are not adjacent in the transverse direction of the wave front. Correspondingly, the valleys L of the adjacent wave fronts, e.g. the wave fronts R3, R4, are not opposed to each other, i.e. the valleys L of the adjacent wave fronts are not adjacent in the transverse direction of the wave front. This means that there is a transition between the location of the valleys L of the adjacent wave fronts R3, R4. This can be observed in FIG. 3 in particular and in FIG. 5 as well. Such a non-opposition according to the preferred embodiments improves the contact, as the contact points have spread out more evenly, not just into lines and columns. The transition equals half a wave.

In a preferred embodiment, the above mentioned non-opposition is implemented such that there is a transition between adjacent wave fronts, e.g. between the wave fronts R2, R3, in such a manner that the protrusions H of the wave front R2 are opposed to the valleys L of the adjacent wave front R3.

The transversal wave fronts TR1 to TR32 have a similar structure. Thus, the protrusions H of the adjacent transversal wave fronts, e.g. the wave fronts TR16 and TR17, are not opposed to each other, i.e. the protrusions H of the adjacent transversal wave fronts are not adjacent in the transverse direction of the transversal wave fronts. Correspondingly, the valleys L of the adjacent transversal wave fronts, e.g. the wave fronts TR16 and TR17, are not opposed to each other, i.e. the valleys L of the adjacent transversal wave fronts are not adjacent in the transverse direction of the transversal wave fronts. This means that there is a transition between the location of the valleys L of the transversal wave fronts TR16, TR17. Thus, there is a transition between the adjacent transversal wave fronts, e.g. the wave fronts TR16 and TR17, in such a manner that the protrusions of the transversal wave front TR16 are opposed to the valleys of the adjacent transversal wave front TR17. This can be seen in FIG. 4 in particular, but also in FIG. 5. The transition equals half a wave.

Said preferred embodiments of the wave fronts R1 to R7 and the transversal wave fronts TR1 to TR32 make the location of the protrusions H symmetrical, which further improves the contact.

It is obvious to a person skilled in the art that as technology develops, the basic idea of the invention can be implemented in a variety of ways. Consequently, the invention and the embodiments thereof are not restricted to the above examples, but may be modified within the scope of the claims.

What is claimed is:

1. An electrode structure for measuring a biosignal from a living body, said electrode structure comprising:
   a contact surface for placement against the body, said contact surface being formed with a plurality of protrusions that define an upper level and a plurality of valleys that define a lower level, each of said plurality of protrusions having a peak located within said upper level, said contact surface being curved at said peak of each of said plurality of protrusions,
   wherein said plurality of protrusions and said plurality of valleys are arranged to define a plurality of adjacent wave fronts.

2. An electrode structure as claimed in claim 1, wherein said plurality of protrusions and said plurality of valleys are successive and alternating to form said plurality of adjacent wave fronts.

3. An electrode structure as claimed in claim 1, wherein said plurality of protrusions and said plurality of valleys are configured to define a plurality of transversal wave fronts which transverse said plurality of adjacent wave fronts in a direction.

4. An electrode structure as claimed in claim 1, wherein said plurality of protrusions and said plurality of valleys are successive and alternating to form said plurality of transversal wave fronts.

5. An electrode structure as claimed in claim 1, wherein said plurality of protrusions are nonadjacently arranged in a direction that is transverse to said plurality of adjacent wave fronts.

6. An electrode structure as claimed in claim 1, wherein said plurality of valleys are nonadjacently arranged in a direction that is transverse to said plurality of adjacent wave fronts.

7. An electrode structure as claimed in claim 1, wherein there is a transition between at least one pair of said plurality of adjacent wave fronts such that said plurality of protrusions of a first adjacent wave front are adjacent to said plurality of valleys of a second adjacent wave front in a direction that is transverse to said plurality of adjacent wave fronts.

8. An electrode structure as claimed in claim 3, wherein said plurality of protrusions are nonadjacently arranged in the direction of said plurality of transversal wave fronts.

9. An electrode structure as claimed in claim 3, wherein said plurality of valleys are nonadjacently arranged in the direction of said plurality of transversal wave fronts.

10. An electrode structure as claimed in claim 3, wherein there is a transition between at least one pair of said plurality of adjacent wave fronts such that said plurality of protrusions of a first adjacent wave front are adjacent to said plurality of valleys of a second adjacent wave front in a direction that is transverse to said plurality of adjacent wave fronts.

11. An electrode structure as claimed in claim 1, wherein said contact surface is an electrically conducting material.

12. An electrode structure as claimed in claim 1, wherein at least one of said plurality of adjacent wave fronts has a substantially sinusoidal form.

13. An electrode structure as claimed in claim 12, wherein said sinusoidal form has a ratio of wavelength over amplitude in a range from about 75 to 100.

14. An electrode structure as claimed in claim 12, wherein said sinusoidal form has a ratio of wavelength over amplitude of about 94.

15. An electrode structure as claimed in claim 3, wherein at least one of said plurality of transversal wave fronts has a substantially sinusoidal form.

16. An electrode structure as claimed in claim 15, wherein said sinusoidal form has a ratio of wavelength over amplitude in a range from about 75 to 100.

17. An electrode structure as claimed in claim 15, wherein said sinusoidal form has a ratio of wavelength over amplitude of about 80.

18. An electrode structure as claimed in claim 15, wherein at least one of said plurality of adjacent wave fronts has a substantially sinusoidal form.

* * * * *